US008877281B2

(12) United States Patent
Segall et al.

(10) Patent No.: US 8,877,281 B2
(45) Date of Patent: Nov. 4, 2014

(54) PREPARATION OF CANOLA PROTEIN ISOLATE INVOLVING ISOELECTRIC PRECIPITATION

(75) Inventors: Kevin I. Segall, Winnipeg (CA); Randy Williardsen, Roseville, CA (US); Martin Schweizer, Winnipeg (CA)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 2258 days.

(21) Appl. No.: 11/524,431

(22) Filed: Sep. 21, 2006

(65) Prior Publication Data
US 2007/0065567 A1    Mar. 22, 2007

Related U.S. Application Data

(60) Provisional application No. 60/718,754, filed on Sep. 21, 2005.

(51) Int. Cl.
| A23L 1/20 | (2006.01) |
| A23L 2/66 | (2006.01) |
| C07K 14/415 | (2006.01) |
| A23J 1/14 | (2006.01) |

(52) U.S. Cl.
CPC ............... *A23J 1/14* (2013.01); *A23V 2002/00* (2013.01); *A23L 1/2005* (2013.01); *A23L 2/66* (2013.01); *C07K 14/415* (2013.01)
USPC .......................................... 426/634; 426/656

(58) Field of Classification Search
USPC ................... 426/656, 589; 530/377
See application file for complete search history.

(56) References Cited

U.S. PATENT DOCUMENTS

| 3,758,452 A | 9/1973 | Owen |
| 4,111,927 A | 9/1978 | Satterlee |
| 4,169,090 A | 9/1979 | Murray et al. |
| 4,208,323 A | 6/1980 | Murray et al. |
| 4,285,862 A | 8/1981 | Murray et al. |
| 5,844,086 A | 12/1998 | Murray |
| 6,005,076 A | 12/1999 | Murray |
| 6,905,713 B2 * | 6/2005 | Diosady et al. ............... 424/755 |
| 2003/0125526 A1 | 7/2003 | Barker et al. |
| 2004/0034200 A1 * | 2/2004 | Logie et al. .................. 530/377 |
| 2004/0254353 A1 | 12/2004 | Barker et al. |
| 2005/0181112 A1 * | 8/2005 | Schweizer et al. ............ 426/656 |

FOREIGN PATENT DOCUMENTS

| CA | 1182112 | 5/1985 | |
| GB | 1540376 | 2/1979 | |
| JP | 55124457 | 9/1980 | |
| WO | WO 02/089598 A1 * | 11/2002 | ............... A23J 1/14 |
| WO | WO 2005/067729 | 7/2005 | |

OTHER PUBLICATIONS

A. Rajendran and P. Neelamegam "Measurement of conductivity of liquids using AT89C55WD microcontroller" vol. 35, issue 1, Jan. 2004, pp. 59-63.*
NPL Soft Drink : www.britishsoftdrinks.com, 2000 (Waybackmachine record, yr 2000).*

* cited by examiner

*Primary Examiner* — Humera Sheikh
*Assistant Examiner* — Bhaskar Mukhopadhyay
(74) *Attorney, Agent, or Firm* — Sim & McBurney; Michael I. Stewart

(57) ABSTRACT

Canola protein isolates consisting predominantly of 7S canola proteins are formed by isoelectric precipitation from aqueous salt solution extracts of canola oil seed meal. Canola protein isolates consisting predominantly of 2S canola protein are recovered from supernatant from the isoelectric precipitation step.

12 Claims, No Drawings

PREPARATION OF CANOLA PROTEIN ISOLATE INVOLVING ISOELECTRIC PRECIPITATION

REFERENCE TO RELATED APPLICATION

This Application claims priority under 35 USC 119(e) from U.S. Provisional patent application Ser. No. 60/718,754 filed Sep. 21, 2005.

FIELD OF INVENTION

The present invention is concerned with the preparation of protein isolates from oil seed meals, particularly canola oil seed meal.

BACKGROUND OF THE INVENTION

In U.S. Pat. Nos. 5,844,086 and 6,005,076 ("Murray II"), assigned to the assignee hereof and the disclosures of which are incorporated herein by reference, there is described a process for the isolation of protein isolates from oil seed meal having a significant fat content, including canola oil seed meal having such content. The steps involved in this process include solubilizing proteinaceous material from oil seed meal, which also solubilizes fat in the meal and removing fat from the resulting aqueous protein solution. The aqueous protein solution may be separated from the residual oil seed meal before or after the fat removal step. The defatted protein solution then is concentrated to increase the protein concentration while maintaining the ionic strength substantially constant, after which the concentrated protein solution may be subjected to a further fat removal step. The concentrated protein solution then is diluted to cause the formation of a cloud-like mass of highly aggregated protein molecules as discrete protein droplets in micellar form. The protein micelles are allowed to settle to form an aggregated, coalesced, dense, amorphous, sticky gluten-like protein isolate mass, termed "protein micellar mass" or PMM, which is separated from the residual aqueous phase and dried.

The protein isolate has a protein content (as determined by Kjeldahl or equivalent method N×6.25) of at least about 90 wt %, is substantially undenatured (as determined by differential scanning calorimetry) and has a low residual fat content. The term "protein content" as used herein refers to the quantity of protein in the protein isolate expressed on a dry weight basis. The yield of protein isolate obtained using this procedure, in terms of the proportion of protein extracted from the oil seed meal which is recovered as dried protein isolate was generally less than 40 wt %, typically around 20 wt %.

The procedure described in the aforementioned patents was developed as a modification to and improvement on the procedure for forming a protein isolate from a variety of protein source materials, including oil seeds, as described in U.S. Pat. No. 4,208,323 (Murray IB), the disclosure of which is incorporated herein by reference. The oil seed meals available in 1980, when U.S. Pat. No. 4,208,323 issued, did not have the fat contamination levels of canola oil seed meals at the time of Murray II patents, and, as a consequence, the procedure of U.S. Pat. No. 4,208,323 cannot produce from such oil seed meals processed according to the Murray II process, proteinaceous materials which have more than 90 wt % protein content. There is no description of any specific experiments in U.S. Pat. No. 4,208,323 carried out using rapeseed (canola) meal as the starting material.

U.S. Pat. No. 4,208,323 itself was designed to be an improvement on the process described in U.S. Pat. Nos. 4,169,090 and 4,285,862 (Murray IA), incorporated herein by reference, by the introduction of the concentration step prior to dilution to form the PMM. The latter step served to improve the yield of protein isolate from around 20% for the Murray IA process.

In copending U.S. patent application Ser. No. 10/137,391 filed May 3, 2002 (US Patent Application Publication No. 20030125526) and U.S. patent application Ser. No. 10/476,230 filed Jun. 9, 2004 (US Patent Application Publication No. 20040254353) (WO 02/089597), assigned to the assignee hereof and the disclosures of which are incorporated herein by reference, there is described a process for producing a protein isolate of high purity, containing at least about 100 wt % protein (N×6.25). In the aforementioned U.S. patent application, the protein isolate is made by a process in which oil seed meal is extracted with a food grade salt solution, the resulting protein solution, after an initial treatment with a colourant adsorbent, if desired, is concentrated to a protein content of at least about 200 g/L, and the concentrated protein solution is diluted in chilled water to form protein micelles, which are allowed to settle to form an aggregated, coalesced, dense amorphous, sticky gluten-like protein isolate mass, termed "protein micellar mass" or PMM, which is separated from residual aqueous phase and may be used as such or dried.

In one embodiment of the process described above and as specifically described in U.S. patent application Ser. Nos. 10/137,391 and 10/476,320, the supernatant from the PMM settling step is processed to recover a protein isolate comprising dried protein from wet PMM and supernatant. This procedure may be effected by initially concentrating the supernatant using ultrafiltration membranes, mixing the concentrated supernatant with the wet PMM and drying the mixture. The resulting canola protein isolate has a high purity of at least about 90 wt %, preferably at least about 100 wt %, protein (N×6.25).

In another embodiment of the process described above and as specifically described in U.S. patent application Ser. Nos. 10/137,391 and 10/476,230, the supernatant from the PMM settling step is processed to recover a protein from the supernatant. This procedure may be effected by initially concentrating the supernatant using ultrafiltration membranes and drying the concentrate. The resulting canola protein isolate has a high purity of at least about 90 wt %, preferably at least about 100 wt %, protein (N×6.25).

The procedures described in the aforementioned U.S. patent applications are essentially batch procedures. In copending U.S. patent application Ser. No. 10/298,678 filed Nov. 19, 2002 (US Patent Application Publication No. 20040039174) (WO 03/043439), assigned to the assignee hereof and the disclosure of which is incorporated herein by reference, there is described a continuous process for making canola protein isolates. In accordance therewith, canola oil seed meal is continuously mixed with a salt solution, the mixture is conveyed through a pipe while extracting protein from the canola oil seed meal to form an aqueous protein solution, the aqueous protein solution is continuously separated from residual canola oil seed meal, the aqueous protein solution is continuously conveyed through a selective membrane operation to increase the protein content of the aqueous protein solution to at least about 200 g/L while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is removed from the settling vessel and may be dried. The PMM has a protein content of at least about 90 wt % (N×6.25), preferably at least about 100 wt %.

In such procedures, canola protein isolate is recovered by dilution with chilled water of a concentrated protein solution to precipitate PMM. In addition, further canola protein isolate may be recovered from the supernatant from the PMM precipitation step.

As described in copending U.S. patent application Ser. No. 11/038,086 (US Patent Application Publication No. 20050181112) (WO 2005/067729), assigned to the assignee hereof and the evidence of which is incorporated herein by reference, the supernatant from the PMM precipitation step may be heat-treated to cause precipitation of 7S and 12S proteins from the supernatant. The 2S protein subsequently recovered from the heat-treated supernatant, has a improved solubility in aqueous media at a variety of pH values and is able to provide improved clarity in solution with soft drinks, thereby providing clear protein fortified soft drinks.

SUMMARY OF INVENTION

It has now been surprisingly found that, if the concentrated canola protein solution is acidified, a canola protein isolate is precipitated which is compositionally similar to the canola protein isolate obtained by the PMM route and then, following separation of the precipitated canola protein isolate, the supernatant can be processed to obtain a further canola protein isolate which is compositionally similar to that obtained from the supernatant from PMM precipitation. This procedure, therefore, represents an alternative manner of obtaining canola protein isolates from the concentrated protein solution. One benefit which results from the isoelectric precipitation procedure is that there is produced a canola protein isolate which has a considerably higher water-binding capacity than the PMM-derived protein isolate.

In an alternative procedure according to another aspect of this invention, PMM may be converted to an isoelectric precipitate by resuspending the PMM in aqueous salt solution and acidifying the resulting solution. The PMM may be resuspended from a wet pellet or, less preferably, from dried isolate. This procedure produces an isoelectric precipitated canola protein isolate which has a much higher water binding capacity than the PMM material which is converted to the isoelectric precipitate.

In another aspect of the invention, the isoelectric precipitation is effected prior to the concentration step and the supernatant from the isoelectric precipitation is processed to recover further protein isolate therefrom.

Accordingly, in one aspect of the present invention, there is provided a process of preparing a protein isolate, which comprises (a) extracting an oil seed meal to cause solubilization of protein in the oil seed meal and to form an aqueous protein solution having a pH of about 5 to about 6.8; (b) separating the aqueous protein solution from residual oil seed meal; (c) acidifying the aqueous protein solution to precipitate therefrom a protein isolate having a protein content of at least about 90 wt % (N×6.25); and (d) separating the precipitated protein isolate from supernatant.

The present invention is particularly concerned with the preparation of a canola protein isolate. Accordingly, in another aspect of the present invention, there is provided a process of preparing a canola protein isolate, which comprises (a) extracting a canola oil seed meal to cause solubilization of canola protein in the canola oil seed meal and to form an aqueous protein solution having a pH of about 5 to about 6.8; (b) separating the aqueous protein solution from residual canola oil seed meal; (c) acidifying the aqueous protein solution to a pH of about 3 to about 4 to precipitate therefrom a canola protein isolate having a protein content of at least about 90 wt % (N×6.25) and consisting predominantly of 7S canola protein; and (d) separating the precipitated canola protein isolate from supernatant.

In accordance with a further aspect of the present invention, there is provided a process of preparing a protein isolate, which comprises (a) extracting an oil seed meal to cause solubilization of protein in the oil seed meal and to form an aqueous protein solution having a pH of about 5 to about 6.8; (b) separating the aqueous protein solution from the residual oil seed meal; (c) increasing the protein concentration of the aqueous protein solution while maintaining the ionic strength substantially constant by using a selective membrane technique to provide a concentrated protein solution; (d) diluting the concentrated protein solution into chilled water having a temperature of below about 15° C. to cause the formation of discrete protein particles in the aqueous solution in the form of micelles; (e) settling the protein miscelles to form an amorphous, sticky, gelatinous, gluten-like protein micellar mass; (f) separating the protein micellar mass from supernatant, the protein micellar mass having a protein content of at least about 90 wt %, preferably at least about 100 wt % (N×6.25); (g) forming an aqueous solution of the protein micellar mass; (h) acidifying the aqueous solution of protein micellar mass to precipitate therefrom a protein isolate having a protein content of at least about 90 wt %, preferably at least about 100 wt % (N×6.25); and (i) separating the precipitated protein isolate from supernatant.

The canola protein isolates produced according to the process herein may be used in conventional and novel applications of protein isolates, such as, protein fortification of processed foods, emulsification of oils, body formers in baked goods and foaming agents in products which entrap gases. In addition, the protein isolate may be formed into protein fibers, useful in meat analogs, and may be used as an egg white substitute or extender in food products where egg white is used as a binder. As can be seen from the data presented below, the isoelectric precipitated canola protein isolate finds particular use as a water binder/thickener. The supernatant-derived canola protein isolate finds particular use in acidified beverage, including clear protein fortified soft drinks. The canola protein isolates may be used as nutritional supplements. Other uses of the canola protein isolates are in pet foods, animal feed and in industrial and cosmetic applications and in personal care products.

GENERAL DESCRIPTION OF THE INVENTION

The initial step of the process of separating the canola protein isolate involves solubilizing proteinaceous material from oil seed meal, particularly canola meal, although the process may be applied to other oil seed meals, such as soybean, traditional rapeseed, traditional flax, Linola®, sunflower and mustard oil seed meals. The invention is more particularly described herein with respect to canola seed meal.

The proteinaceous material recovered from canola seed meal may be the protein naturally occurring in canola seed or the proteinaceous material may be a protein modified by genetic manipulation but possessing characteristic hydrophobic and polar properties of the natural protein. Canola oil seed is also known as rapeseed or oil seed rape.

Protein solubilization is effected most efficiently by using a food grade salt solution since the presence of the salt enhances the removal of soluble protein from the oil seed meal. Where the canola protein isolate is intended for non-food uses, non-food grade chemicals may be employed. The food grade salt usually is sodium chloride, although other salts, such as, potassium chloride, may be used. The food grade salt solution has an ionic strength of at least about 0.05, preferably at least about 0.1, to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the oil seed meal chosen.

An antioxidant may be present in the aqueous food grade salt solution. The antioxidant may be any convenient antioxidant, such as sodium sulfite or ascorbic acid. The quantity of the antioxidant employed in the solubilization step may vary from about 0.01 to about 1 wt %, preferably about 0.05 wt %. The antioxidant serves to inhibit oxidation of phenolics present in the aqueous protein solution.

In a batch process, the salt solubilization of the protein is effected at a temperature of at least about 5° and preferably up to about 35° C., preferably accompanied by agitation to decrease the solubilization time, which is usually about 10 to about 60 minutes. It is preferred to effect the solubilization to extract substantially the maximum amount of protein from the oil seed meal, so as to provide an overall high product yield.

The lower temperature limit of about 5° C. is chosen since solubilization is impractically slow below this temperature while the upper preferred temperature limit of about 35° C. is chosen since the process becomes uneconomic at higher temperature levels in a batch mode.

In a continuous process, the extraction of the protein from the canola oil seed meal is carried out in any manner consistent with effecting a continuous extraction of protein from the canola oil seed meal. In one embodiment, the canola oil seed meal is continuously mixed with a salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially the maximum amount of protein from the canola oil seed meal. The solubilization in the continuous procedure preferably is effected at elevated temperatures, preferably above about 35° C., generally up to about 65° C. or more.

The aqueous salt solution and the canola oil seed meal have a natural pH of about 5 to about 6.8. pH values of about 5.3 to about 6.2 are preferred.

The pH of the food grade salt solution may be adjusted to any desired value within the range of about 5 to about 6.8 for use in the extraction step by the use of any convenient food grade acid, usually hydrochloric acid, or food grade alkali, usually sodium hydroxide, as required. Where the canola protein isolate is intended for non-food uses, then non-food grade chemicals may be used.

The concentration of oil seed meal in the food grade salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The aqueous phase resulting from the extraction step then may be separated from the residual canola meal, in any convenient manner, such as by employing a decanter centrifuge, followed by disc centrifugation and/or filtration to remove residual meal. The separated residual meal may be dried for disposal.

The colour of the final canola protein isolate can be improved to obtain a lighter and less intense yellow colour by the mixing of powdered activated carbon or other pigment adsorbing agent with the separated aqueous protein solution and subsequently removing the adsorbent, conveniently by filtration, to provide a protein solution. Diafiltration of the separated aqueous protein solution, before or after concentration, as described below, also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

Where the canola seed meal contains significant quantities of fat, as described in the aforementioned U.S. Pat. Nos. 5,844,086 and 6,005,076, then the defatting steps described therein may be effected on the separated aqueous protein solution and on the concentrated aqueous protein solution discussed below. When the colour improvement step is carried out, such step may be effected after the first defatting step.

As an alternative to extracting the oil seed meal with an aqueous food grade salt solution, such extraction may be made using water alone, although the utilization of water alone tends to extract less protein from the oil seed meal than the aqueous food grade salt solution. Where such alternative is employed, then the food grade salt, in the concentrations discussed above, may be added to the protein solution after separation from the residual oil seed meal in order to maintain the protein in solution during the concentration step described below. When a colour removal step and/or a first fat removal step is carried out, the food grade salt generally is added after completion of such operations.

The aqueous protein solution then is concentrated to increase the protein concentration thereof while maintaining the ionic strength thereof substantially constant. Such concentration generally is effected to provide a concentrated protein solution having a protein concentration of between 10 and about 300 g/L or higher, preferably about 50 to about 100 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 3,000 to about 100,000 daltons, preferably about 5,000 to about 10,000, having regard to differing membrane materials and configurations, and, for continuous operation, dimensioned to permit the desired degree of concentration as the aqueous protein solution passes through the membranes.

The concentrated protein solution then may be subjected to a diafiltration step using an aqueous salt solution of the same molarity and pH as the extraction solution. Such diafiltration may be effected using from about 2 to about 20 volumes of diafiltration solution, preferably about 5 to about 10 volumes of diafiltration solution. In the diafiltration operation, further quantities of contaminants are removed from the aqueous protein solution by passage through the membrane with the permeate. The diafiltration operation may be effected until no significant further quantities of phenolics and visible colour are present in the permeate. Such diafiltration may be effected using a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentration step and diafiltration step may be effected at any convenient temperature, generally about 20° to about 60° C., preferably about 20° to about 30° C., and for the period of time to effect the desired degree of concentration. The temperature and other conditions used to some degree depend upon the membrane equipment used to effect the concentration and the desired protein concentration of the solution.

As is well known, ultrafiltration and similar selective membrane techniques permit low molecular weight species to pass therethrough while preventing higher molecular weight species from so doing. The low molecular weight species include not only the ionic species of the food grade salt but also low molecular weight materials extracted from the source material, such as, carbohydrates, pigments and anti-nutritional factors, as well as any low molecular weight forms of the protein. The molecular weight cut-off of the membrane is usually chosen to ensure retention of a significant proportion of the protein in the solution, while permitting contaminants to pass through having regard to the different membrane materials and configurations.

The concentrated and optionally diafiltered protein solution may be subject to a further defatting operation, if required, as described in U.S. Pat. Nos. 5,844,086 and 6,005,076.

The concentrated and optionally diafiltered protein solution may be subject to a colour removal operation as an alternative to the colour removal operation described above. Powdered activated carbon may be used herein as well as granulated activated carbon (GAC). Another material which may be used as a colour adsorbing agent is polyvinyl pyrrolidone.

The colour absorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinyl pyrrolidone is used as the colour adsorbing agent, an amount of about 0.5% to about 5% w/v, preferably about 2% to about 3% w/v, may be used. The colour adsorbing agent may be removed from the canola protein solution by any convenient means, such as by filtration.

The concentrated and optionally diafiltered protein solution resulting from the optional colour removal step may be subjected to pasteurization to kill any bacteria which may have been present in the original meal as a result of storage or otherwise and extracted from the meal into the canola protein isolate solution in the extraction step. Such pasteurization may be effected under any desired pasteurization conditions. Generally, the concentrated and optionally diafiltered protein solution is heated to a temperature of about 55° to about 70° C., preferably about 60° to about 65° C., for about 10 to about 15 minutes, preferably about 10 minutes. The pasteurized concentrated protein solution then may be cooled for further processing as described below, preferably to a temperature of about 25° to about 40° C.

The optimum protein concentration of the concentrated and optionally diafiltered and optionally pasteurized aqueous protein solution is about 5 to about 10 wt %, since higher concentrations result in viscosities which make it difficult to acidify the solution uniformly and to separate solids precipitated in the acidification step. This optimal protein concentration may be achieved by concentrating the aqueous protein solution to the required concentration, or by first concentrating the aqueous protein solution to a higher concentration of about 20 to about 25 wt % or higher and then diluting the concentrated protein solution to the about 5 to about 10 wt % range with aqueous food grade salt solution.

For the formation of an isoelectric precipitate as provided herein, the concentrated and optionally diafiltered and optionally pasteurized protein solution should have a conductivity of at least about 1 mS, preferably about 10 to about 20 mS.

The concentrated and optionally diafiltered and optionally pasteurized protein solution then is acidified at a temperature of about 10° to about 70° C., preferably about 20° to about 40° C., to a pH of about 3.0 to about 4.0, preferably about 3.5, using any convenient acid, such as hydrochloric acid, to cause the formation of a precipitate of canola protein isolate. The precipitate is recovered from the supernatant and may be dried by any convenient technique, such as spray drying, freeze drying or vacuum drum drying to provide a canola protein isolate. The dried isoelectric precipitation (IP)-derived canola protein isolate has a high protein content of at least about 90 wt % (N×6.25), preferably at least about 100 wt %.

If desired, the isoelectric precipitation step may be effected directly on the canola protein solution without effecting a concentration step. One or more of the optional steps of colour removal, diafiltration and pasteurization described above may be effected on the canola protein solution prior to the isoelectric precipitation step. The precipitated canola protein isolate is recovered from supernatant and dried.

The supernatant from the isoelectric precipitation contains significant amounts of canola protein, not precipitated in the precipitation step, and is processed to recover therefrom canola protein isolate predominantly in the form of 2S protein. The supernatant from the acidification step, following removal of the isoelectric precipitate, may be concentrated to increase the protein concentration thereof. Such concentration is effected using any convenient selective membrane technique, such as ultrafiltration, using membranes with a suitable molecular weight cut-off permitting low molecular weight species, including the salt and other non-proteinaceous low molecular weight materials extracted from the protein source material, to pass through the membrane, while retaining canola protein in the solution. Ultrafiltration membranes having a molecular weight cut-off of about 3,000 to 100,000 daltons, preferably about 5,000 to about 10,000 daltons, having regard to differing membrane materials and configuration, may be used. Concentration of the supernatant in this way also reduces the volume of liquid required to be dried to recover the protein. The supernatant generally is concentrated to a protein concentration of about 100 to about 400 g/L, preferably about 200 to about 300 g/L, prior to drying.

Such concentration operation may be carried out in a batch mode or in a continuous operation, as described above for the protein solution concentration step.

The concentrated supernatant may be subjected to a diafiltration step using water as the extraction solution to effect removal of salt and other contaminants from the concentrated supernatant. Such diafiltration may be effected using about 2 to about 20 volumes of water, preferably about 5 to about 10 volumes of water. Such diafiltration may be effected using a membrane having a molecular weight cut-off in the range of about 3,000 to about 100,000 daltons, preferably about 5,000 to about 10,000 daltons, having regard to different membrane materials and configurations.

An antioxidant may be present in the diafiltration medium during at least part of the diafiltration step. The antioxidant may be any convenient antioxidant, such as sodium sulfite or ascorbic acid. The quantity of antioxidant used in the diafiltration medium may vary from about 0.01 to about 1 wt %, preferably about 0.05 wt %.

The concentrated and optionally diafiltered supernatant may be dried by any convenient technique, such as spray drying, freeze drying or vacuum drum drying, to a dry form to provide a further canola protein isolate. Such further canola protein isolate has a high protein content, in excess of about 90 wt %, preferably at least about 100 wt % protein (calculated as Kjeldahl N×6.25).

If desired, the supernatant may be subjected to a heat-treatment step as described in the aforementioned U.S. patent application Ser. No. 11/038,086 to cause precipitation from the supernatant of 7S protein and any 12S protein present and to recover a 2S protein isolate having an increased proportion of 2S protein.

Such heat treatment may be effected using a temperature and time profile sufficient to decrease the proportion of 7S present in the concentrated supernatant, preferably to reduce the proportion of 7S protein by a significant extent. In general, the 7S protein content of the supernatant is reduced by at least about 50 wt %, preferably at least about 75 wt % by the heat treatment. In general, the heat treatment may be effected at a temperature of about 70° to about 100° C., preferably about 75° to about 95° C., for about 2 to about 30 minutes, preferably about 5 to about 15 minutes. The precipitated 7S protein may be removed in any convenient manner, such as centrifugation or filtration The heat-treatment operation may be effected prior to concentration of the supernatant, but preferably following the concentration step. The heat treatment step may be effected on the supernatant obtained from the isoelectric precipitation step or may be effected following adjustment of the pH of the supernatant to less acid values, since the 7S and 12S proteins are more prone to degradation and hence precipitation at such less acid values. The pH of the supernatant may be adjusted to a pH of about 5 to about 6.8, preferably about 5.8 to about 6.2. Such pH adjustment may be carried out using any convenient alkalinizing agent, such as aqueous sodium hydroxide. Following such heat treatment, the pH may be adjusted to more acid values, preferably in the range of about 5 to about 10 wt %.

In addition, the supernatant prior to concentration or post-concentration, and/or pre-heat treatment or post-heat treatment, may be subjected to a colour removal operation to improve the colour of the final product, as an alternative to or as an additional step to the colour removal operation described above, using any convenient pigment absorbing agent, such as a powdered activated carbon granular activated carbon and/or polyvinyl pyrrolidone in the quantities described above.

If desired, at least a portion of the wet isoelectric precipitate may be combined with at least a portion of the concentrated supernatant prior to drying the combined protein streams by any convenient technique to provide a combined canola protein isolate composition. The relative proportions of the proteinaceous materials mixed together may be chosen to provide a resulting canola protein isolate composition having a desired profile of 2S/7S/12S proteins. Alternatively, the dried protein isolates may be combined in any desired proportions to provide any desired specific 2S/7S/12S protein profiles in the mixture. The combined canola protein isolate composition has a high protein content, in excess of about 90 wt %, preferably at least about 100 wt %, (calculated as Kjeldahl N×6.25).

In another alternative procedure, where a portion only of the concentrated supernatant is mixed with a part only of the isoelectric precipitate and the resulting mixture dried, the remainder of the concentrated supernatant may be dried as any of the remainder of the isoelectric precipitate. Further, dried isoelectric precipitate and dried supernatant also may be dry mixed in any desired relative proportions, as discussed above.

By operating in this manner, a number of canola protein isolates may be recovered, in the form of dried isoelectric precipitate, dried supernatant and dried mixtures of various proportions by weight of isoelectric precipitation-derived canola protein isolate and supernatant-derived canola protein isolate, generally from about 5:95 to about 95:5 by weight, which may be desirable for attaining differing functional and nutritional properties based on the differing proportions of 2S/7S/12S proteins in the compositions.

As noted previously, the isoelectric precipitation derived canola protein while having a protein content of at least about 90 wt % (N×6.25), preferably at least about 100 wt %, may be produced from PMM produced by diluting the concentrated and optionally diafiltered and optionally pasteurized protein solution according to the procedures of the aforementioned U.S. patent application Ser. Nos. 10/137,391 and 10/476,630.

The PMM, preferably in the wet form but also possibly in dried form, is solubilized in a food grade salt solution, such as sodium chloride solution, having an ionic strength of at least about 0.05, preferably at least about 0.1, preferably at ambient temperatures, although elevated temperatures may be employed, to form an aqueous protein solution, generally having a protein concentration of about 1 to about 30 wt % or higher, preferably about 5 to about 10 wt %. The resulting aqueous protein solution then is subjected to the isoelectric precipitation steps discussed above.

As also discussed above and as demonstrated in the Examples below, the isoelectric precipitated canola protein isolate has a much higher water-binding capacity than the PMM-derived canola protein isolate. Employing this procedure permits there to be produced a highly-soluble canola protein isolate, being the canola protein isolate derived from supernatant from the PMM precipitation step, and a canola protein isolate of high water-binding capacity by conversion of the PMM to an isoelectric precipitate.

EXAMPLES

Example 1

This Example illustrates the preparation of canola protein isolate according to one embodiment of the invention.

150 kg of commercial canola oil seed meal was added to 1000 L of 0.1 M NaCl at 60° C. and agitated for 5 minutes to provide an aqueous protein solution.

The clarified canola protein solution, having a protein content of 16.8 g/L, was reduced in volume to 60 L by concentration at 60° C. on an ultrafiltration system having polyvinyldiene difluoride (PVDF) and polyethersulfone (PES) membranes having molecular weight cut-offs of 5,000 and 10,000 daltons respectively (UF1). The ultrafiltered canola protein solution was then diafiltered five times at 60° C. on a diafiltration system using PVDF and PES membranes having molecular weight cut-off membranes of 5,000 and 10,000 daltons, respectively, using 0.1 M NaCl solution containing 0.05 wt % ascorbic acid to a final volume of 45 L with a protein content of 174.7 g/L.

A 4 L sample of the concentrated and diafiltered canola protein solution (UF1 retentate) was combined with 12 L of 0.1 NaCl to adjust the protein concentration to 46.8 g/L. Concentrated HCL was added to the diluted solution at 22° C. until the pH of the acidified canola protein solution was 3.5 to effect isoelectric precipitation.

The sample became cloudy and was allowed to sit for 15 minutes. The sample then was centrifuged in batches of 4×1 L at 7100 g for 15 minutes to collect the precipitate. The collected precipitate (IEP precipitate) was separated from supernatant and freeze dried. The dried precipitate (C302) was found to have a protein content of 102.43 wt % (N×6.25) d.b. (Percentage protein values were determined using a LECO FP 328 Nitrogen Determinator).

Approximately 16 L of supernatant from the centrifugation (IEP supernatant) were concentrated to 3 L on an ultrafiltration system (UF2) using a PES membrane having a molecular weight cut-off of 100,000 daltons. The concentrated supernatant then was diafiltered on a diafiltration system using a PES membrane having a molecular weight cut-off of 100,000 daltons with 9 volumes of water to a final volume of 3.5 L with a protein content of 72.1 g/L. The protein solution was spray dried.

The dried protein (C202) was found to have a protein content of 104.05 wt % (N×6.25) d.b.

Example 2

This Example describes the preparation of samples of canola protein isolate by the procedure of the aforementioned U.S. patent application Ser. No. 10/137,391.

'a' kg of canola meal was added to 'b' L of 0.1 M NaCl solution at 60° C., and continuously extracted with a 5 minute hold time to provide an aqueous protein solution. The residual canola meal was removed and the resulting protein solution was clarified by centrifugation and filtration to produce 'c' L of filtered protein solution having a protein content of 'd' % by weight.

A 'e' L aliquot of the protein extract solution was reduced in volume to 'f' L by concentration on a ultrafiltration system using PVDF and PES membranes having molecular weight cut-offs of 5,000 and 10,000 daltons respectively and then diafiltered with 'g' L of 0.1M NaCl solution containing 0.05% ascorbic acid. The resulting concentrated protein solution had a protein content of 'h' % by weight.

The concentrated solution (less the portion removed for isoelectric precipitation) at 'i' ° C. was diluted 'j' into cold RO water having a temperature 'k' ° C. A white cloud formed immediately and was allowed to settle. The upper diluting water was removed and the precipitated, viscous, sticky mass (PMM) was recovered from the bottom of the vessel in a yield of '1' wt % of the filtered protein solution. The dried PMM derived protein was found to have a protein content of 'm' % (N×6.25) d.b. The product was given a designation 'n' (C300).

The parameters "a" to "n" are set forth in the following Table I:

TABLE I

| n | BW-AL022-H23-04A | BW-AL022-L15-04A |
|---|---|---|
| a | 150 | 22.5 |
| b | 1000 | 150 |
| c | 847 | 95 |
| d | 1.68 | 2.01 |
| e | 847 | 95 |
| f | 60 | 5 |
| g | 300 | 25 |
| h | 17.47 | 21.85 |
| i | 29.6 | 30 |
| j | 1:10 | 1:10 |
| k | 2.4 | 3 |
| l | 33.24 | 41.88 |
| m | 105.45 | 106.67 |

The removed diluting water was reduced in volume to 'o' L by ultrafiltration using PES membranes having a molecular weight cut-off of 10000 daltons. The concentrate contained 'p' % protein by weight. With the additional protein recovered from the supernatant, the overall protein recovery of the filtered protein solution was 'q' wt %. The concentrate was spray dried to form a final product given designation 'n' (C200) and had a protein content of 'r' % (N×6.25) d.b.

The parameters "n" to "r" are set forth in the following Table II.

TABLE II

| n | BW-AL022-H23-04A |
|---|---|
| o | 23.5 |
| p | 7.27 |
| q | 45.26 |
| r | 98.99 |

Example 3

This Example provides analysis of the protein isolates produced by isoelectric precipitation (C302) and from the resulting supernatant (C202).

The isoelectric precipitate produced by the process of Example 1 was insoluble in water and hence its protein profile could not be determined by HPLC. However, HPLC analysis for 12S, 7S and 2S canola proteins was effected on the materials provided at several stages of the procedure and the results are summarized in the following Table III. The protein profiles are expressed as a percentage of the total peak area attributable to protein.

TABLE III

Protein Profile of Various Fractions

| Sample | % 12S | % 7S | % 2S |
|---|---|---|---|
| Adjusted UF 1 retentate | 7.9 | 82.6 | 9.6 |
| IEP precipitate | Could not be analyzed | | |
| IEP supernatant | 0.6 | 11.2 | 88.2 |
| Concentrated and diafiltered IEP supernatant | 1.0 | 18.6 | 80.4 |
| IEP UF 2 composite permeate | Contained no protein | | |
| IEP UF 2 diafiltration permeates | Contained no protein | | |
| C302 | Could not be analyzed | | |
| C202 | 1.1 | 17.2 | 81.7 |

As can be seen from this data, the isoelectric precipitation caused a large drop in the proportion of 12S and 7S in solution. It is believed that these species were precipitated but that the low pH environment caused the 12S and 7S proteins to dissociate into smaller subunits which eluted overlapping the 2S peak.

Qualitative SDS-PAGE analysis of the AL022-H23-04A products was conducted to provide more insight into their composition. The C302 was not completely soluble in the electrophoresis buffer and so a portion of the sample did not enter the gel and remained at the origin. The bands that were resolved for the C302 showed the presence of mainly 7S/12S, with a lower concentration of 2S, similar to what was observed in the analysis of the C300. The C202 and the C200 both dissolved completely and so could be compared reliably. It appeared that the proportion of 7S/12S remaining in the C202 was higher than that observed in the C200. This is contrary to the results of the HPLC analysis, and confirms the hypothesis that in the HPLC analysis, some broken down 7S/12S is co-eluting with the 2S. The results of the HPLC analysis is set forth in the following Table IV:

TABLE IV

Protein profile (HPLC) of supernatant derived isolates

| Sample | % 12S | % 7S | % 2S |
|---|---|---|---|
| C202 (Example 1) | 1.1 | 17.2 | 81.7 |
| C200 (Example 1) | 1.2 | 25.1 | 73.7 |

The colours of the C302 and C202 isolates were fairly dark but were still similar to the C300 and C200 respectively, prepared as described in Example 2. The results obtained using a Minota CR310 chroma meter attached to a DP301 data processor are set forth in the following Table V:

TABLE V

Lab Colour Values for C302 and C202

| Sample | L | a | b |
|---|---|---|---|
| C302 | 63.53 | 2.44 | 19.63 |
| C300 | 66.57 | 2.09 | 22.17 |
| C202 | 74.27 | 1.62 | 16.66 |
| C200 | 73.79 | 1.69 | 17.68 |

Example 4

This Example compares the solubility of the protein produced by isoelectric precipitation (C302) and from the resulting supernatant (C202) produced in accordance with Example 1, with those derived from PMM (C300) and from supernatant from PMM precipitation (C200), produced according to the procedure of Example 2.

Solubility was determined using a method based on Morr et al, J. Food Sci., 50:1715-1718. Sufficient protein powder to supply 0.5 g of protein was weighed into a beaker and then a small amount of reverse osmosis (RO) purified water was added and the mixture stirred until a smooth paste formed. Additional water then was added to bring the volume to approximately 45 ml. The contents of the beaker were then slowly stirred for 60 minutes using a magnetic stirrer.

The pH of each sample was determined immediately after dispersing the protein and then adjusted to values of 4, 5, 6 or 7 using NaOH or HCL. The pH was measured and corrected twice during the 60 minutes of stirring. Following completion of the stirring, the sample was made up to 50 ml total volume with RO water, yielding a 1% w/v protein dispersion. An aliquot of the protein dispersion was reserved for protein content determination. Another portion of the sample was centrifuged at 8000 g for 10 minutes, which sedimented any undissolved material and yielded a clear supernatant. The protein content of the supernatant then was determined and the solubility calculated as follows:

Solubility (%)=(supernatant protein concentration/ original dispersion protein concentration)×100

In addition, the solubility of the C302 and C202 samples in 0.1 M NaCl was determined using the above-described procedure, substituting the saline for water.

The solubility of the C302 sample in water and 0.1 M NaCl as well as the C300 sample in water is set forth respectively in the following Tables VI and VII:

TABLE VI

Solubility of C302 versus C300 in Water

| pH | C302 Solubility (%) | C300 Solubility (%) |
|---|---|---|
| 4 | 8.7 | 83.0 |
| 5 | 10.4 | 63.5 |
| 6 | 6.3 | 18.3 |
| 7 | 8.1 | 84.6 |

TABLE VII

Solubility of C302 in 0.1 M NaCl

| pH | Solubility (%) |
|---|---|
| 4 | 0 |
| 5 | 1.5 |
| 6 | 8.0 |
| 7 | 3.8 |

As can be seen from these Tables, the solubility of the C302 sample was poor in both water and 0.1 M saline regardless of pH. The solubility of the C302 sample in water was much worse than the C300.

The solubility of the C202 sample in water and in 0.1 M NaCl as well as the C200 sample in water is set forth respectively in the following Tables VIII and IX:

TABLE VIII

Solubility of C202 versus C200 in Water

| pH | C202 Solubility (%) | C200 Solubility (%) |
|---|---|---|
| 4 | 91.6 | 100.0 |
| 5 | 95.6 | 97.8 |
| 6 | 54.1 | 97.7 |
| 7 | 46.9 | 95.0 |

TABLE IX

Solubility of C202 in 0.1 M NaCl

| pH | Solubility (%) |
|---|---|
| 4 | 70.8 |
| 5 | 65.9 |
| 6 | 66.0 |
| 7 | 67.2 |

As can be seen from this data, the solubility of the C202 sample was much better than the C302 sample. The solubility of the C202 sample in water was comparable to the C200 sample at pH 4 and 5, but inferior at pH 6 and 7.

Example 5

This Example illustrates the foaming properties of C302 and C202 canola protein isolate samples produced according to the procedure of Example 1 and in comparison to C300 and C200 canola protein isolate samples produced according to the procedure of Example 2.

Sufficient protein powder to supply 7.5 g of protein was weighed out into a beaker. A small amount of 0.075 M NaCl solution was stirred into the protein powder to make a paste. Enough saline solution to make the volume up to approximately 140 ml was then added and the mixture stirred with a magnetic stirrer. Stirring speed was controlled so as to try to avoid foam formation. After 10 minutes of stirring, the pH of the solution was adjusted to a value of 7 using NaOH or HCl as necessary. The mixture was then stirred for a further 10 minutes and the pH corrected. The sample was then made up to 150 ml with 0.075 M NaCl to yield a 5% w/v dispersion.

A sample of protein dispersion (75 ml) was poured into the bowl of the Hobart N-50 mixer (Hobart Corporation, Troy, Ohio) and whipped for 15 minutes on the highest speed (setting 3) of the mixer using the whisk attachment. Every 5 minutes whipping was stopped and two measuring cups (125 ml) were filled with foam and weighed. These foam samples were then returned to the bowl before whipping proceeded. Overrun was calculated for each timepoint using the following equation (Phillips et al, J. Food Sci., 55(5); 1441-1444, 1453):

Overrun (%)=[(wt liquid sample (125) ml)−wt foam (125 ml))/wt foam (125 ml)]×100

To measure foam stability, a second sample (75 ml) of protein dispersion was poured into the special bowl of the Hobart N-50 mixer and whipped for 15 minutes on the highest speed (setting 3) of the mixer using the whisk attachment. The special bowl contains a 6 mm diameter hole drilled into the bottom of the bowl just outside the path of the beater. During whipping this hole was covered by a piece of tape. Once whipping was completed the tape was removed and the hole cleared with a stirring rod. The weight of material that drained out of the bowl was determined every 5 minutes for 15 minutes. The weight of drained sample was divided by the starting weight of foam to calculate what percentage of material had drained out of the bowl.

The foam overrun and foam stability for C302 are set forth respectively in Tables X and XI:

TABLE X

| Foam Overrun for C302 | |
| --- | --- |
| Whipping time (min) | Overrun (%) |
| 5 | 304.4 |
| 10 | 315.0 |
| 15 | 311.1 |

TABLE XI

| Foam Stability for C302 | |
| --- | --- |
| Drainage time (min) | Mass Loss (%) |
| 5 | 16.7 |
| 10 | 27.2 |

TABLE XI-continued

| Foam Stability for C302 | |
| --- | --- |
| Drainage time (min) | Mass Loss (%) |
| 15 | 33.7 |

As can be seen, the C302 product exhibited poor foam formation and poor foam stability, which can be attributed to the poor solubility of the same, as seen from Example 3.

The foam overrun and foam stability for C202 in comparison to C200 are in the following Tables XII and XIII:

TABLE XII

| Foam Overrun for C202 versus C200 | | |
| --- | --- | --- |
| Whipping Time (min) | C202 Overrun (%) | C200 Overrun (%) |
| 5 | 1707.6 | 3118.9 |
| 10 | 2178.8 | 3110.9 |
| 15 | 2357.4 | 3211.2 |

TABLE XIII

| Foam Stability for C202 versus C200 | | |
| --- | --- | --- |
| Drainage Time (min) | C202 Mass Loss (%) | C200 Mass Loss (%) |
| 5 | 0 | 0 |
| 10 | 0 | 0 |
| 15 | 0 | 0.5 |

As may be seen from these Tables, the C202 had good foaming properties, with high overrun and excellent stability. However, the foam volume was inferior to that of C200. The appearance of the C202 foam was also inferior to that of C200. C200 formed a smooth foam, while the C202 foam appeared to be drier and had some undispersed protein particles, likely due to the partial solubility of C202 in saline at pH7.

Example 5

Example illustrates the emulsifying activity of C302 and C202 canola protein isolate samples produced according to the procedures of Example 1.

Sufficient protein powder to supply 1.5 g of protein was made up to 150 g with the addition of RO water. The sample was processed with a Silverson mixer at 4500 rpm until the protein was fully dispersed. The pH of the sample was then adjusted to pH 7 using NaOH or HCl as necessary. Canola oil (150 g) was added to yield a mix that was 50% w/w oil and 0.5% w/w protein. Emulsification of the mix was achieved by processing with a Silverson mixer at 5000 rpm for 5 minutes.

A sample of the emulsion was diluted 1:500 in 0.1% SDS solution and the absorbance read at 500 nm (done at least in duplicate). The moisture content of the emulsion sample was also calculated. The turbidity and emulsifying activity index ($m^2$ fat droplet surface area stabilized/g protein) were then calculated as detailed in Hill (1996) Emulsions. In: Methods of Testing Protein Functionality. Hall, G. M. (ed). pp. 153-185.

The emulsifying activity of samples C302, C300, C202 and C200 are set forth in the following Table XIV.

TABLE XIV

Emulsifying Activity of Samples

| Sample | Emulsifying Activity (m²/g) |
|---|---|
| C302 | 6.9 |
| C300 | 24.5 |
| C202 | 14.6 |
| C200 | Not determined |

As may be seen from this data, the C302 sample had a very poor emulsifying activity, notably worse than the C300 sample.

Example 7

This Example illustrates the water-binding capacity of C302 and C202 samples produced according to the procedure of Example 1 in comparison to the C300 and C200 samples produced according to the procedure of Example 2.

Protein powder (1 g) was weighed into centrifuge tubes (50 ml) of known weight. To this powder was added 20 ml of deionized water at natural pH. The contents of the tubes were mixed using a vortex mixer at moderate speed for 1 minute. The samples were then incubated at room temperature for a total of 10 minutes with 30 seconds of vortex mixing provided after five and ten minutes. Next, the samples were centrifuged at 1000 g for 15 minutes at 20° C. After centrifugation the supernatant was carefully poured off, ensuring that all solid material remained in the tube. The centrifuged tube was then re-weighed and the weight of water saturated sample was determined.

Water binding capacity (WBC) was calculated as:

WBC (ml/g)−(mass of wet sample−mass of dry sample)/(mass of dry sample×total solids content of sample)

The water binding capacity of the C302 and C202 samples in comparison to the C300 and C200 samples is set forth in the following Table XV:

TABLE XV

Water Binding Capacity of C302 and C202

| Sample | Water Binding Capacity (ml/g) |
|---|---|
| C302 | 7.35 |
| C300 | 1.35 |
| C202 | 0.00 |
| C200 | 0.00 |

As may be seen from this data, the water binding capacity of the C302 sample was excellent and far higher than for the C300 sample. As noted in Example 3, the C202 and C200 samples are highly soluble in water and hence the weight of material left in the tube after draining the water was less than the original weight of the protein powder. The water binding capacity of these samples, therefore, is zero.

Example 8

This Example illustrates the oil-binding capacity of C302 and C202 samples produced in accordance with Example 1 in comparison to C300 and C200 samples produced in accordance with Example 2.

Oil binding capacity was assessed by the same method as the water binding capacity described in Example 6 except that 20 ml of oil was used in place of the 20 ml of water and the oil binding capacity (OBC) was calculated as:

OBC (ml/g)=[(mass of wet sample−mass of dry sample)/density of oil]/(mass of dry sample×total solids content of sample)

The results obtained for C302 and C202 samples in comparison to C300 and C200 samples are set forth in the following Table XVI:

TABLE XVI

Oil Binding Capacity of C302 and C202

| Sample | Oil Binding Capacity (ml/g) |
|---|---|
| C302 | 2.83 |
| C300 | 3.26 |
| C202 | 5.36 |
| C200 | 3.49 |

As may be seen from this data, the oil binding capacity of the C202 sample was better than that for the C200 sample, while the oil binding capacity of the C302 was slightly poorer than that of the C300 sample.

Example 9

This Example illustrates the preparation of an isoelectric precipitate from PMM produced according to the procedure of Example 2.

A PMM-containing dilution pellet from process run BW-AL022-L15-04A (100.47 g, 23.15% protein), effected following the procedure described in Example 2, was combined with 0.1 M NaCl solution (364.73 g) to yield a sample having a protein content of 4.54%. The pH of the solution was lowered from the initial value of 6.02 to 3.50 using 5% HCl. The sample was allowed to sit quiescently for 15 minutes and then was centrifuged at 7100 g for 15 minutes to separate the precipitated protein from the supernatant. The wet precipitate (26.01 g) was freeze dried to produce 5.45 g of C302 protein. The protein content of the C302 protein was 90.17% on a wet basis (moisture content not determined), indicating the protein was an isolate.

The water binding capacity of the C302 protein was determined following the procedure of Example 7 in comparison to the C300 protein from the same run. The results are set forth in the following Table XVII:

TABLE XVII

Water binding capacity of various products

| Sample | Water binding capacity (ml/g) |
|---|---|
| AL022-L15-04A C302 | 8.51* |
| AL022-L15-04A C300 | 1.14 |

*Note that the moisture content of the C302 was not determined and was assumed to be 2% for the calculation of the water binding capacity As may be seen from this Table, the C302 product bound more water than the C300 protein made in the same batch and exhibited the same high water binding capacity as exhibited by the C302 protein in Example 7 in comparison to the C300 product.

Example 10

This Example illustrates effecting the isoelectric precipitation on the aqueous protein solution without a concentration step and processing the supernatant to recover canola protein isolate which is predominantly 2S protein.

15 kg of canola oil seed meal was extracted with 150 L of 0.15 M NaCl by stirring at room temperature for 30 minutes. The extract was separated from the spent meal by passage through a decanter and the extract further clarified by sequential passage through filter pads with pore sizes of 2.0 µm and 0.8 µm. The pH of the filtrate was then lowered from an initial value of 5.66 to 3.5 by the addition of 2M HCl, which resulted in the formation of a precipitate that was removed by sequential passage of the sample through filter pads with pore sizes of 2.0 µm and 0.8 µm. The precipitate was not recovered in this experiment.

The supernatant from the isoelectric precipitation was then concentrated on a small membrane unit using a PES membrane with a MWCO of 10,000 Da. The sample was reduced in volume from 106 L to approximately 5 L. The concentrated sample was then diafiltered with 7 volumes of pH 3.5 water to reduce the salt content. The diafiltered retentate was then split into three samples.

The first sample (control) was pasteurized at 60° C. for 10 minutes, cooled to 25° C., centrifuged at 10200 g for 10 minutes and filtered through #3 (extra-fine) filter pads. The second sample was heat treated at 85° C. for 10 min., cooled to 25° C., centrifuged at 10200 g for 10 minutes and filtered followed through #3 filter pads. The pH of the third sample was raised to 6 by the addition of aqueous sodium hydroxide, the sample was heat-treated at 80° C. for 10 minutes and then cooled to 25° C. Precipitate formed was recovered by centrifugation at 10200 g for 10 minutes following by filtration through #3 filter pads. The three products were then spray dried and coded C202 (control), C202H pH 3.5 (heat treated at pH 3.5) and C202H pH 6 (heat treated at pH 6).

Process samples were analyzed for free phenolics (absorbance at 330 nm), visible colour (absorbance at 390 nm), protein content (LECO) and/or protein profile (SEC HPLC). The HPLC chromatograms for acidified samples were difficult to interpret as the low pH conditions convert 7S and 12S into smaller subunits that elute overlapping with the 2S peak. Final products were also analyzed for moisture content (oven method), dry colour (Minolta colourimeter) and solutions were prepared for wet colour analysis. Protein powder (0.35 g) was dissolved in water (10 ml) using a vortex mixer. For the C202 pH 6 product, the pH of the wet colour sample was lowered to 4 by the addition of HCl. The visible colour of the wet samples was assessed by A390, the clarity by the absorbance at 600 nm and the pH measured.

The isoelectric precipitation step resulted in the removal of 46% of the nitrogen from the clarified extract. The protein profile of the filtrate before acidification was 48.9% 7S: 1.7% 12S: 49.4% 2S and was 2.0% 7S: 0.4% 12S: 97.6% 2S after removal of the isoelectric precipitate. It is believed that 7S and 12S were the primary species precipitated, but their removal may not be as complete as the HPLC data indicates. As mentioned above, low pH conditions cause the conversion of 7S and 12S into subunits that elute overlapping with the 2S peak. Therefore, some of the "2S" in the acidified sample may be degraded 7S and 12S. Heat treatment of the concentrated sample at pH 3.5 caused a slight increase in cloudiness but no significant precipitate formation. Heat treatment at pH 6 resulted in the precipitation of a significant amount of protein.

All of the C202 products produced were isolates as shown in Table XVIII.

TABLE XVIII

Yield and protein content of C202 products

| Sample | Wt obtained (g) | Protein content (w.b.) (%) | Moisture Content (%) | Protein content (d.b.) (%) |
|---|---|---|---|---|
| C202 control | 108 | 89.52 | 6.47 | 95.71 |
| C202H pH 3.5 | 102 | 90.59 | 5.21 | 95.57 |
| C202H pH 6 | 58 | 89.77 | 4.46 | 93.96 |

The dry colour of C202 products is shown in Table XIX. The results were fairly similar although the sample heat treated at pH 3.5 was redder and less yellow than the control sample. The C202H pH 6 sample, which was more depleted in 7S and 12S compared to the other samples, was the lightest, the most green (least red) and also less yellow than the control.

TABLE XIX

Dry colour of C202 products

| Sample | L | a | b |
|---|---|---|---|
| C202 control | 85.39 | −1.49 | 22.49 |
| C202H pH 3.5 | 85.45 | −1.07 | 20.76 |
| C202H pH 6 | 86.02 | −1.69 | 20.86 |

The wet colour of the C202 samples appeared quite similar. The clarity of the C202H pH 6 sample appeared the best. When assessed by absorbance measurements, the C202H pH 6 sample was found to be the lightest and the clearest. However, the differences between the three samples were fairly minor and all were acceptable (Table XX). The clarity of all the samples was found to remain stable when the samples were cooled to refrigerator temperatures.

TABLE XX

Analysis of wet colour samples

| Sample | pH | A390 | A600 |
|---|---|---|---|
| C202 control | 3.71 | 1.75 | 0.213 |
| C202H pH 3.5 | 3.78 | 1.94 | 0.297 |
| C202H pH 6 adjusted to pH 4 | 4.00 | 1.04 | 0.160 |

Example 11

This Example illustrates the functionality of the supernatant-derived canola protein isolates prepared as described in Example 10 for solubility, foam overrun and foam stability.

Samples of canola protein isolates prepared as described in Example 10 were assessed for functionality.

Solubility:

Product solubility was determined using a method based on that reported by Morr et al. Sufficient protein powder to supply 0.5 g of protein was weighed into each of five beakers and then a small amount of reverse osmosis (RO) purified water was added to each sample and the mixtures stirred until smooth pastes formed. Additional water was then added to bring the volume of the samples to approximately 40 ml. The contents of the beakers were then slowly stirred for 60 minutes using a magnetic stirrer. The pH was determined immediately after dispersing the protein, one sample was stirred at native pH and the others adjusted to pH 4, 5, 6 or 7 with NaOH or HCl. The pH of the adjusted samples was measured and corrected two times during the 60 minutes of stirring. After the 60 minutes of stirring, the samples were made up to 50 ml total volume with RO water, yielding 1% w/v protein dispersions. An aliquot of each protein dispersion was reserved for protein content determination by LECO. Another portion of the samples was centrifuged at 7800 g for 10 minutes. This sedimented any undissolved material and yielded a clear supernatant. The protein content of the supernatant was then determined.

Solubility (%)=(supernatant protein conc./Original dispersion protein conc.)×100

The solubility of the C202 control is set forth in the following Table XXI:

TABLE XXI

Solubility for C202 control

| pH | Solubility (%) |
|---|---|
| Natural (3.68) | 96.4 |
| 4 | 100 |
| 5 | 100 |
| 6 | 94.9 |
| 7 | 92.7 |

As may be seen from this Table, the solubility of the C202 control was found to be very good over the entire pH range considered.

Foam Overrun:

Sufficient protein powder to supply 8 g of protein was weighed out into a beaker. A small amount of water was stirred into the protein powder to make a paste. Enough water to make the volume up to approximately 150 ml was then added and the mixture stirred with a magnetic stirrer. Stirring speed was controlled so as to try to avoid foam formation. After approximately 20 minutes of stirring the pH of the solution was adjusted to a value of 7 using NaOH or HCl as necessary. The mixture was then stirred for a further 10 minutes and the pH corrected. The sample was then made up to 160 ml with water to yield a 5% w/v dispersion.

A sample of protein dispersion (75 ml) was poured into the bowl of the Hobart N-50 mixer (Hobart Corporation, Troy, Ohio) and whipped for 5 minutes on the highest speed (setting 3) of the mixer using the whisk attachment. After 2, 3.5 and 5 minutes of whipping, the mixer was stopped and two measuring cups (125 ml) were filled with foam and weighed. These foam samples were then returned to the bowl before whipping proceeded. Overrun was calculated for each time-point using the following equation (Phillips et al).

Overrun (%)=[(wt liquid sample (125 ml)−wt foam (125 ml))/wt foam (125 ml)]×100

Foam Stability:

To measure foam stability, a second sample (75 ml) of protein dispersion was poured into the special bowl of the Hobart H-50 mixer and whipped for 5 minutes on the highest speed (setting 3) of the mixer using the whisk attachment. The special bowl contains a 6 mm diameter hole drilled into the bottom of the bowl just outside the path of the beater (Phillips et al, 1990). During whipping this hole was covered by a piece of tape. Once whipping was completed the tape was removed and the hole cleared with a stirring rod. The weight of material that drained out of the bowl was determined every 5 minutes for 15 minutes. The weight of drained sample was divided by the starting weight of foam to calculate what percentage of material had drained out of the bowl.

The effect of whipping time on overrun for C202 products is set forth in the following Table XXII:

TABLE XXII

Effect of whipping time on overrun for C202 produts

| Whipping time (minutes) | Overrun (%) C202 | Overrun (%) C202H pH 6 |
|---|---|---|
| 2 | 3078 | 2957 |
| 3.5 | 3090 | 3211 |
| 5 | 3070 | 3069 |

The foaming properties of the C202 products tested were excellent, with high overruns (Table XXII) and good stability. For the C202 control and C202H pH 6 samples, no mass loss was recorded during the 15 minutes period after whipping the foam. The stability of the C202 control was observed to be better than the C202H pH 6 sample as the latter sample had a drop of liquid hanging from the bowl at the 15 minutes mark while no droplet formation was evident in the control sample after the same length of time.

Example 12

This Example illustrates effecting isoelectric precipitation on the aqueous protein solution without a concentration step and the recovery of a canola protein isolate which is predominantly 7S protein and processing the supernatant to recover a canola protein isolate which is predominantly 2S protein.

180 g of canola meal was extracted with 1800 ml of 0.15 M NaCl by stirring at room temperature for 30 minutes with an overhead stirrer. The extract was separated from the spent meal by centrifugation at 7100 g for 10 minutes and the extract further clarified by filtration through one set of #3 (extra-fine) filter pads. The pH of the filtrate was then lowered from an initial value of 5.72 to 3.5 by the addition of 6M HCl and the sample allowed to stand for 15 minutes. The precipitate formed was removed by centrifugation at 7100 g for 10 minutes and then freeze dried. This product was coded C302.

The isoelectric supernatant was further clarified by passage through one set of #3 filter pads. The clarified supernatant was then concentrated on a Vivaflow membrane unit equipped with a Hydrosart membrane with a MWCO of 10000 Da. The sample was reduced in volume from approximately 950 ml to approximately 26.5 ml. The concentrated sample was then diafiltered with 5 volumes of pH 3.5 water to reduce the salt content. The diafiltered retentate was then split into two samples. The first sample (control) was freeze dried as is (product code C202). The second sample was heat treated at 85° C. for 5 minutes, cooled to 25° C. then freeze dried (product code C202H).

Process samples were analyzed for free phenolics (absorbance at 330 nm), visible colour (absorbance at 390 nm), protein content (LECO) and/or protein profile (SEC HPLC). Note that it is difficult to interpret the HPLC chromatograms for acidified samples as the low pH conditions convert 7S and 12S into smaller subunits that elute overlapping with the 2S peak. Final products were also analyzed for moisture content (oven method), dry colour (Minolta colourimeter) and solutions of C202 and C202H were prepared for wet colour analysis. Protein powder (0.35 g) was dissolved in water (10 ml) using a vortex mixer. The visible colour of the wet samples was assessed by A390 and the clarity by the absorbance at 600 nm.

The isoelectric precipitation step resulted in the removal of 53.7% of the nitrogen from the clarified extract. The protein profile (expressed as a percentage of total protein meal area) of the filtrate before acidification was 62.3% 7S: 3.4% 12S: 34.3% 2S and was 3.0% 7S: 0.8% 12S: 96.2% 2S after removal of the isoelectric precipitate. It is believed that 7S and 12S are the primary species precipitated, but their removal may not be as complete as the HPLC data indicates. As mentioned previously, low pH conditions cause the conversion of 7S and 12S into subunits that elute overlapping with the 2S peak. Therefore, some of the "2S" in the acidified sample may be degraded 7S and 12S. Heat treatment of the concentrated supernatant at pH 3.5 caused a slight increase in cloudiness but no significant precipitate formation.

All of the products generated in this study were isolates, with protein contents (d.b.) greater than 90% (Table XXIII).

TABLE XXIII

Yield and protein content of IEP products

| Sample | Wt obtained (g) | Protein content (w.b.) (%) | Moisture content (%) | Protein content (d.b.) (%) |
|---|---|---|---|---|
| C302 | 7.29 | 91.68 | 5.47 | 96.99 |
| C202 | 2.44 | 84.62 | 6.64 | 90.64 |
| C202H | 2.56 | 85.21 | 6.67 | 91.30 |

The dry colours of the products are shown in Table XXIV. The lightness score for the C302 was good, but the lightness scores for the C202 products were lower. The C302 was more yellow and green than the C202 products. The heat treated C202H was darker and less yellow than the non-heat treated C202.

TABLE XXIV

Dry colour of IEP products

| Sample | L | a | b |
|---|---|---|---|
| C302 | 86.00 | −2.83 | 25.33 |
| C202 | 79.76 | 0.05 | 21.69 |
| C202H | 78.07 | 0.07 | 20.34 |

The C202 and C202H wet colour samples were somewhat hazy. The clarity likely could have been improved by filtering the samples prior to freeze drying as the diafiltration retentate samples were somewhat hazy, particularly after heat treatment (C202H). In terms of visual colour the samples looked similar to the eye. According to the absorbance readings, the C202H had a little more colour than the C202 and also was hazier (Table XXV).

TABLE XXV

Analysis of wet colour samples

| Sample | A390 | A600 |
|---|---|---|
| C202 | 5.52 | 0.825 |
| C202H | 6.79 | 1.054 |

Heat treatment of diafiltered, concentrated supernatant at pH 3.5 appeared to offer no advantages in terms of colour or clarity. Therefore, the heat treatment step was not necessary for these samples.

The water binding capacity of the C302 isolate was determined.

Protein powder (1 g) was weighed into centrifuge tubes (50 ml) of known weight. To this powder was added approximately 20 ml of reverse osmosis purified water at the natural pH. The contents of the tubes were mixed using a vortex mixer at moderate speed for 1 minute. The samples were than incubated at room temperature for a total of 10 minutes with 30 seconds of vortex mixing provided after 5 and 10 minutes. Next, the samples were centrifuged at 1000 g for 15 minutes at 20° C. After centrifugation the supernatant was carefully poured off, ensuring that all solid material remained in the tube. The centrifuge tube was then re-weighed and the weight of water saturated sample was determined.

Water binding capacity (WBC) was calculated as:

WBC (ml/g)=(mass of wet sample−mass of dry sample)/(mass of dry sample×total solids content of sample)

The water binding capacity of the C302 was found to be 2.95 ml/g. This is a lower level than observed for C302 products in previous IEP studies (approximately 5 to 9 ml/g, see, for example, Example 7). The difference may be due to the fact that in this Example, the IEP step was performed on extract instead of more purified streams, such as UF1 retentate dilution pellet or re-solubilized C300. Even though the water binding capacity observed for the C302 in this Example was lower than other C302 products, the value was still higher than that typically observed for C300 products (approximately 1 to 2 ml/g).

SUMMARY OF DISCLOSURE

In summary of this disclosure, isoelectric precipitation has been successfully utilized to produce two novel canola protein isolate products, designated C302 and C202. The C302 and C202 products were similar to C300 and C200 products in colour and purity. The functionality of the C202 product was reminiscent of C200 product. The C302 product is more distinct from the C300 product, with the C302 not as soluble and not performing well as an emulsifier. The C302 product, however, performed extremely well as a water-binding agent, significantly out performing the C300 product. Modifications are possible within the scope of the invention.

What we claim is:

1. A process of preparing a canola protein isolate, which comprises:
   (a) extracting a canola oil seed meal to cause solubilization of canola protein in the canola oil seed meal and to form an aqueous protein solution having a pH of about 5 to about 6.8;
   (b) separating the aqueous protein solution from residual canola oil seed meal;
   (c) acidifying the aqueous protein solution to a pH of about 3 to about 4 to precipitate therefrom a canola protein isolate having a protein content of at least about 90 wt % (N×6.25) and comprising predominantly 7S canola protein;
   (d) separating the precipitated canola protein isolate from supernatant; and
   (e) processing the supernatant to recover therefrom additional canola protein isolate having a protein content of at least about 90 wt % (N×6.25) comprising predominantly 2S canola protein, said processing including heat-treating said supernatant to precipitate 7S and any 12S protein from the supernatant and separating the degraded 7S/12S protein from the heat-treated supernatant, wherein the pH of said supernatant is adjusted to the range of about 5 to about 6.8 prior to said heat treatment step.

2. The process of claim 1 wherein said supernatant is concentrated prior to said heat treatment step.

3. The process of claim 1 wherein said aqueous protein solution has a protein concentration of about 5 to about 10 wt %.

4. The process of claim 1 wherein said aqueous canola protein solution is concentrated while maintaining the ionic strength substantially constant by using a selected membrane technique prior to said acidifying step.

5. The process of claim 4 wherein the aqueous canola protein solution is concentrated to a concentration of about 10 to about 300 g/L.

6. The process of claim 1 wherein said aqueous canola protein solution is concentrated to a concentration of about 20 to about 25 wt % protein and, prior to said acidifying step, the concentration of the canola protein solution is adjusted to about 5 to about 10 wt % by the addition of aqueous salt solution.

7. The process of claim 4 or 6 wherein said aqueous protein solution subjected to the acidifying step has a conductivity of at least about 1 mS.

8. The process of claim 1 wherein said aqueous solution has an ionic strength of about 0.1 to about 0.6 and a pH of about 5.3 to about 6.2.

9. The process of claim 5 wherein said aqueous canola protein solution is concentrated to a concentration of about 50 to about 100 g/L.

10. The process of claim 7 wherein said aqueous protein solution subjected to the acidifying step has a conductivity of about 10 to about 20 mS.

11. The process of claim 1 wherein the pH of supernatant is adjusted to the range of about 5.3 to about 6.2.

12. The process of claim 2 or 1 wherein said supernatant is subjected to a colour removal operation following separation of the degraded 7S/12S protein and prior to recovery of the canola protein isolate comprising predominantly 2S canola protein and/or prior to or following said concentration step.

* * * * *